(12) United States Patent
Dumitrescu et al.

(10) Patent No.: US 6,440,371 B1
(45) Date of Patent: Aug. 27, 2002

(54) REAGENT PACKAGE

(75) Inventors: Nicholae Dumitrescu, Stamford, CT (US); Andrew Oakes, Harrington Park, NJ (US); Randolph Bradshaw, Brewster, NY (US); Robert L. Berger, Bound Brook, NJ (US); William M. Jameson, Cranbury, NJ (US); Chris Robinson, Lawrenceville, NJ (US); James R. Laskey, Chestertown, MD (US)

(73) Assignee: Bayer Corporation, Tarrytown, NY (US)

( * ) Notice: Subject to any disclaimer, the term of this patent is extended or adjusted under 35 U.S.C. 154(b) by 0 days.

(21) Appl. No.: 09/437,516

(22) Filed: Nov. 10, 1999

Related U.S. Application Data (62) Division of application No. 08/985,759, filed on Dec. 5, 1997, now Pat. No. 6,043,097.

(51) Int. Cl.[7] .............................. B01L 11/00
(52) U.S. Cl. .................... 422/101; 422/63; 422/102; 422/103; 422/61
(58) Field of Search .................. 422/99, 101, 102, 422/103, 106, 63–65, 56, 58, 61

(56) References Cited

U.S. PATENT DOCUMENTS

| 4,707,450 A | * 11/1987 | Nason ........................ 422/61 |
| 4,876,068 A | * 10/1989 | Castaneda .................... 422/58 |
| 5,800,782 A | * 9/1998 | Hagstrom et al. ............ 422/75 |
| 5,817,522 A | * 10/1998 | Goodman et al. .......... 436/165 |

* cited by examiner

*Primary Examiner*—Lyle A. Alexander
(74) *Attorney, Agent, or Firm*—Andrew L. Klawitter; John M. Paolino; Rodman & Rodman (57) ABSTRACT

The reagent package includes a container housing section and a container lid that are sealed together to define one or more inside chambers. The reagent package accommodates a filter screen member and a glass ampoule in the container chamber. The glass ampoule contains one reagent ingredient, usually in a dry powder form and the space within the chamber outside the glass ampoule usually contains a reconstituting liquid ingredient. When the reagent package is ready for use a pressure force is imposed on the outside wall of the chamber adjacent the glass ampoule to crush the ampoule and permit the liquid ingredient within the chamber to mix with the powder ingredient released from the glass ampoule.

9 Claims, 10 Drawing Sheets

REAGENT PACKAGE

This application is a divisional application of U.S. Ser. No. 08/985,759 filed Dec. 5, 1997 now U.S. Pat. No. 6,045,097.

BACKGROUND OF THE INVENTION

This invention is directed to reagent packaging devices for storing one or more ingredients or reagents separate from one another in a single reagent package for subsequent mixing in the reagent package, and more particularly to a novel reagent package having a valve controlled opening with a deflectable valve member at the package opening.

Automated sample analysis systems as disclosed in U.S. Pat. Nos. 5,268,167 and 5,399,497 can perform a variety of different tests on a test subject, such as a serum sample, in a relatively short period of time. Generally the serum sample is separated into a predetermined number of segregated portions and a different test is usually performed on each segregated portion of the serum sample. It is thus common practice to divide the serum sample into a series of separate isolated sample segments that correspond to each separate test. The isolated sample segments are enabled to co-act with specific reagents to produce an analyzable reaction that forms the basis for a test result.

Different reagents will produce different test results on respective sample segments and the compendium of the separate test results provide a body of information or data relating to the characteristics of the serum sample.

As used herein, the term reagent is intended to refer to a single reagent, a mixture of two or more reagents and/or a mixture of reagent with a reconstituting liquid.

Reagents for sample analysis systems are preferably used in liquid form to permit allotment of a precise predetermined amount of reagent to each sample segment and to help ensure that the reaction between the reagent and the serum sample is uniform. Generally, the reagent is diluted to a desired concentration before it is permitted to co-act with a serum sample.

It is well known that some reagents used in sample analysis systems have a limited shelf life especially if produced as a solution of one or more reagent components. Therefore, optimum test results between a reagent and a serum sample are usually obtained if the reagent is dissolved or diluted shortly before being used for test purposes.

Since the shelf life of a reagent in dry form is usually longer than the shelf life of the reagent in a liquid condition it is common practice to maintain a reagent in dry condition in a reagent mixing package. In some instances, the mixing package is arranged to hold in segregated condition a dry reagent component and a liquid reconstituting component. When use of the reagent is desired, the components are intermixed within the package One known reagent package such as shown in U.S. Pat. No. 4,515,753 includes a reagent in lyophilized powder form in a first breakable capsule and a reconstituting liquid for the reagent in a second breakable capsule. The capsules are broken by compressing the package to release the contents of each capsule for mixing within the package. An outlet port in the package permits outside access to the mixed ingredients. Although this reagent package provides a freshly mixed reagent for immediate use in a sample analysis system, it is difficult to seal the package once the ingredients have been mixed. This package also does not permit long term preservation of liquid that is openly contained in the package and therefore the reconstituting liquid must be maintained in a capsule.

It is thus desirable to provide a reagent package for one or more reagent components wherein the package has a valve controlled opening and wherein a reconstituting liquid can be openly stored and preserved in the package under a leak-tight seal that is valve controlled and wherein the package can optionally accommodate breakable capsules and a filter screen.

OBJECTS AND SUMMARY OF THE INVENTION

Among the several objects of the invention may be noted the provision of a novel reagent package having a valve controlled opening, a novel reagent package having a valve controlled opening wherein the valve can be locked in a closed position with a locking clip to provide a substantially leak-tight seal, a novel reagent package having a valve controlled opening wherein the valve in a movable condition, without the locking clip provides an evaporation barrier for liquid contained in the package when the valve is in a closed position, a novel reagent package having a valve controlled opening wherein the valve can be rendered movable with respect to the container opening to optionally select open and closed positions of the reagent package, a novel reagent package that can accommodate a breakable ampoule with one reagent and an openly stored reconstituting liquid, a novel reagent package having a valve controlled opening wherein the valve can be locked in a closed position to provide a substantially leak tight seal that permits long term storage of a liquid reagent, a novel reagent package with a breakable ampoule and a filter screen that is structured to resist damage from broken glass, a novel reagent package which can be deformed to break a frangible ampoule inside the package without damaging the package and without damaging a valve provided on the package, a novel reagent package having two separate non-communicable chambers to constitute a dual reagent package, a novel reagent package that provides valve controlled access to substantially all liquid reagent in the package, a novel reagent package that accommodates a breakable ampoule and permits aspiration of reagent from the broken ampoule without the glass particles, and a novel method of providing controlled access to a reagent in a package. Other objects and features of the invention will be in part apparent and in part pointed out hereinafter.

In accordance with the present invention, the reagent package includes a container having an inside chamber and a restrictable opening to the chamber. A valve is positioned on the container to control the opening. The valve has a valve closed position to close off and seal the opening and a valve open position to permit access to the container chamber through the container opening. Preferably the valve is a rocker valve which is pivotable about a pivot axis that is spaced above the container opening.

In a preferred embodiment of the invention the reagent package is a dual package and includes two separate chambers that are non communicable with each other. Each chamber has a separate opening controlled by a separate rocker valve. The rocker valves are identical and have pivots that are cantilevered at the end of pivot support arms to permit deflection between the valve face and the valve pivots.

When the reagent package is in a valve closed position reagent materials inside the container cannot be accessed. Also when the reagent package is in a valve closed position a locking clip can be placed on the package to further secure the valves against the container opening thereby enhancing the valve seal. The locking clip enables the ingredients of the reagent package to be stored without degradation for approximately two years under refrigeration.

In one embodiment of the invention the reagent package includes a filter screen member in each chamber and a breakable glass ampoule in each chamber. The lass ampoule contains one reagent ingredient and is preferably in a dry lyophilized condition. The internal chamber space outside the glass ampoule can accommodate a reconstituting liquid. When it is desired to use the ingredients of the reagent package, a compression force is applied to the outside wall of the reagent package proximate the glass ampoule to crush the ampoule. The contents of the ampoule are thus released and can mix inside the package chamber with the reconstituting liquid. If desired, the ampoule can contain a liquid ingredient.

The reagent package also includes a well portion that defines the lowest point in the package. The well portion receives the filter screen member and also receives the bottom of the filter screen member through which the mixed ingredients of the package are aspirated. The screen member filters out any broken glass during aspiration. As the chamber ingredients are depleted during aspiration of reagent the unused reagent tends to flow into the bottom of the screen member in the well where it can be easily aspirated thus minimizing or eliminating any waste of reagent material.

The invention also includes a method of providing controlled access to a reagent. A closed container is provided with a valve controlled opening to maintain the container in a sealed condition when the valve is in a closed position and to provide access to the container when the valve is in an open position. The method further includes arranging the valve as a rocker valve at the opening of the container such that the valve is pivotable about an axis that is spaced from the container opening. The rocker valve can thus be pivoted from the valve open position to the valve closed position and vice versa. The rocker valve is provided with a valve face having opposite ends. Pivot means for the rocker valve connect to only one end of the valve face in cantilever arrangement. The cantilever arrangement permits the valve face to be deflectable from the pivot axis and permits pressure sealing of the valve face against the opening in the container.

The invention accordingly comprises the constructions and method hereinafter described, the scope of the invention being indicated in the claims.

DESCRIPTION OF THE DRAWINGS

In the accompanying drawings.

Corresponding reference numbers indicate corresponding parts throughout the several views of the drawings.

DETAILED DESCRIPTION OF THE INVENTION

Figure 1:
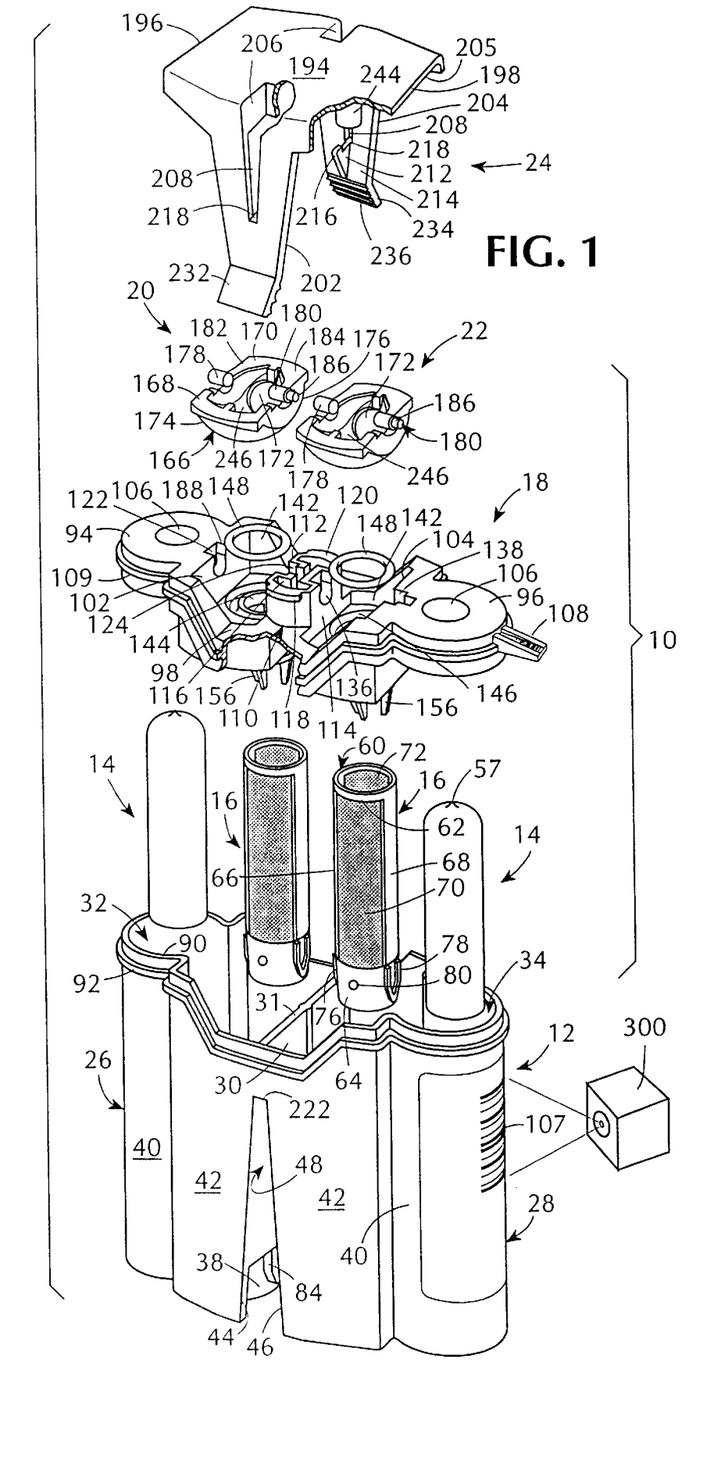
FIG. 1 is an exploded perspective view of a reagent package and a locking clip incorporating one embodiment of the invention.
Figure 2A:
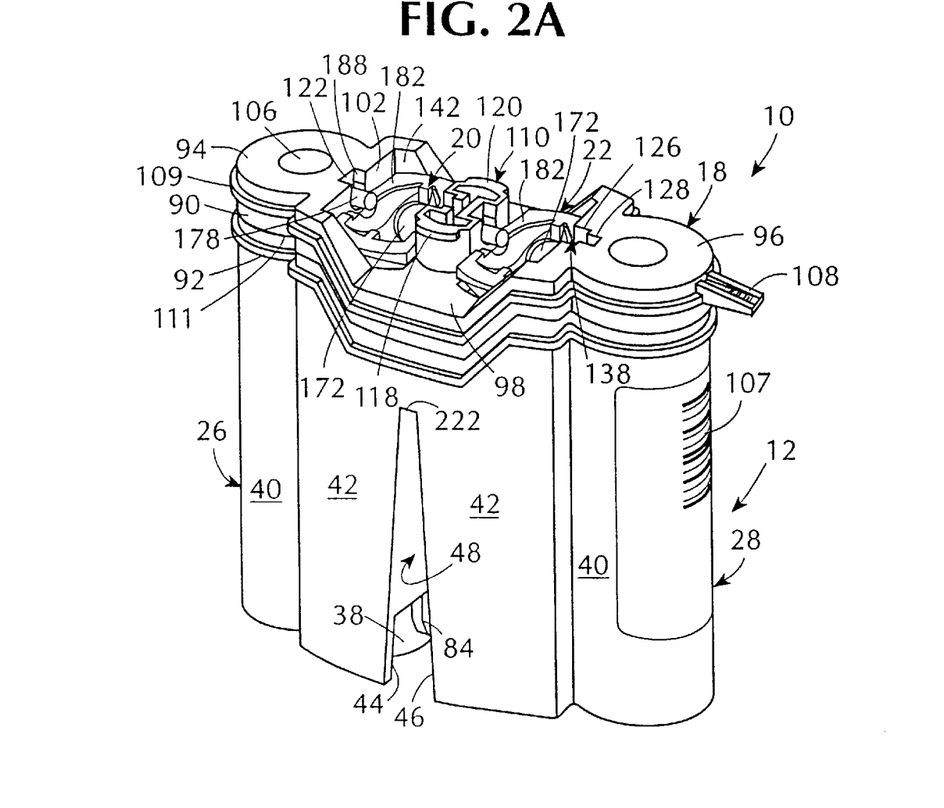
FIG. 2A is a perspective view thereof in assembled condition without the locking clip.

A reagent package incorporating one embodiment of the invention is generally indicated by the reference number 10 in FIGS. 1 and 2A.

The reagent package 10 includes a container housing section 12 that accommodates two glass ampoules 14, 14, two filter screens 16, 16, and a container lid 18 that supports two identical rocker valves 20 and 22. A locking clip member 24 maintains the rocker valves 20 and 22 of the reagent package 10 in a locked and leak-proof condition during shipping and storage.

It should be noted that the reagent package 10 is a dual package with two packaging sections 26 and 28 (FIGS. 2A and 5) arranged side-by-side. Although the packaging sections 26 and 28 are formed as an integral unit of the reagent package 10 the contents of either packaging section 26 and 28 cannot communicate with the contents of the other packaging section. Each packaging section 26 and 28 is similar in structure and function. If desired any of the packaging sections 26 and 28 can be formed as a separate reagent package.

The container housing section 12 includes a partition wall 30 that divides the container interior into two separate container chambers 32 and 34. Each of the container chambers 32 and 34 can accommodate a frangible ampoule 14 and a filter screen 16.

Figure 5:
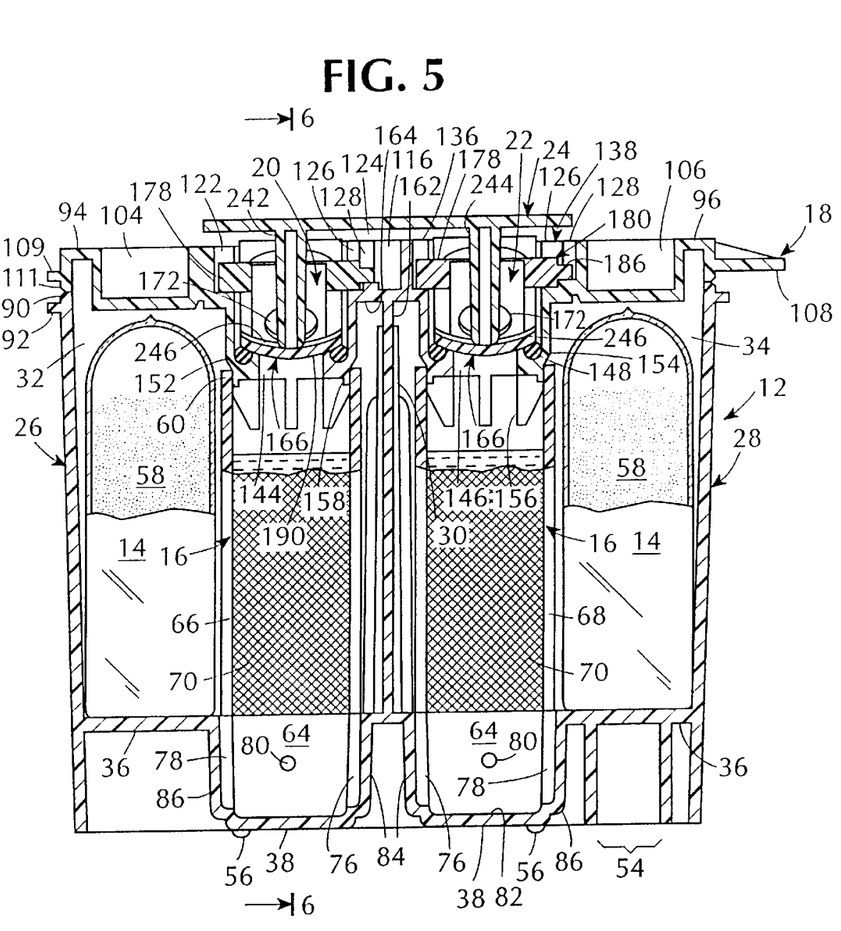
FIG. 5 is a sectional view taken on the line 5—5 of FIG. 4, with a rocker valve thereof in a closed position.
Figure 7:
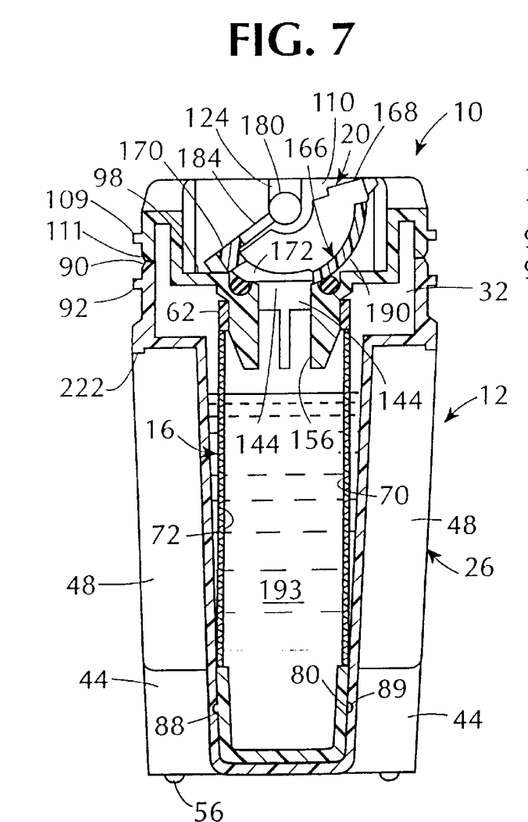
FIGS. 7 and 8 are sectional views similar to FIGS. 5 and 6 with the locking clip removed and the rocker valve in an open position.
Figure 8:
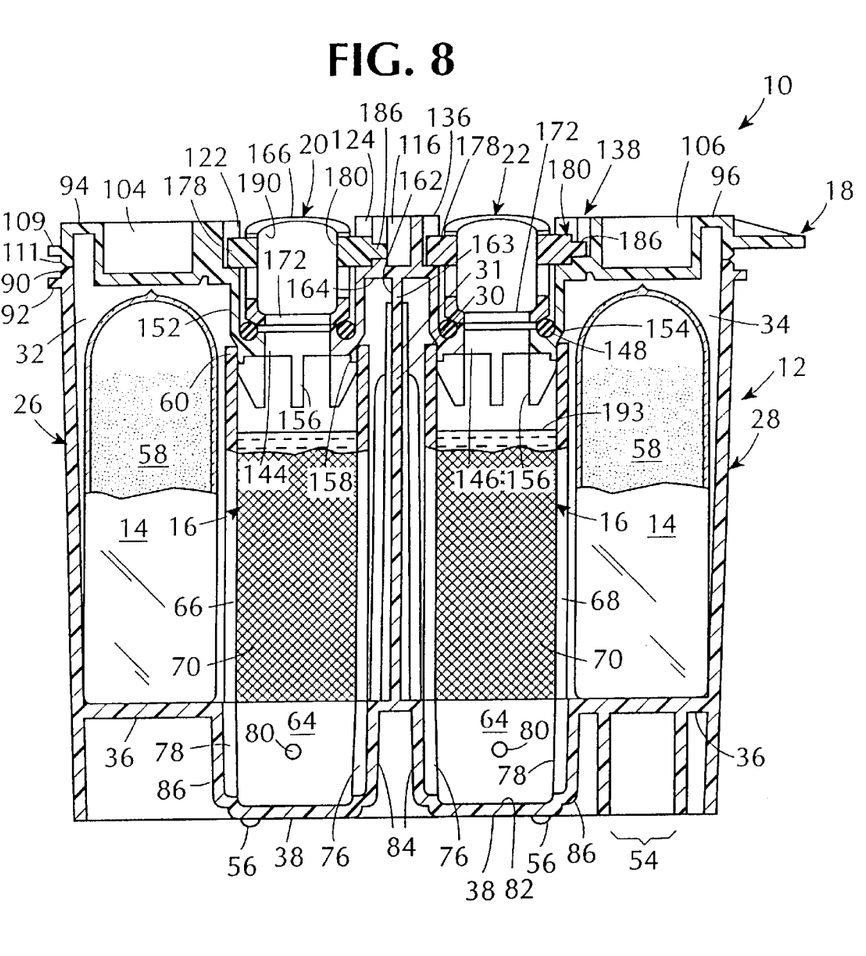

Referring to FIGS. 5 and 8 each container chamber 32 and 34 has an upper stepped base portion 36 that supports the ampoule 14 and a lower stepped base portion 38 that supports the filter screen member 16. A portion 40 (FIGS. 1 and 11) of the container housing section 12 which partially and closely surrounds each ampoule 14 is of generally cylindrical shape whereas a portion 42 of the container housing section 12 that partially confines each filter screen member 16 is of generally trapezoidal shape. The vertical walls of the housing section 12 are slightly inclined as most clearly shown in FIG. 7.

Figure 2B:
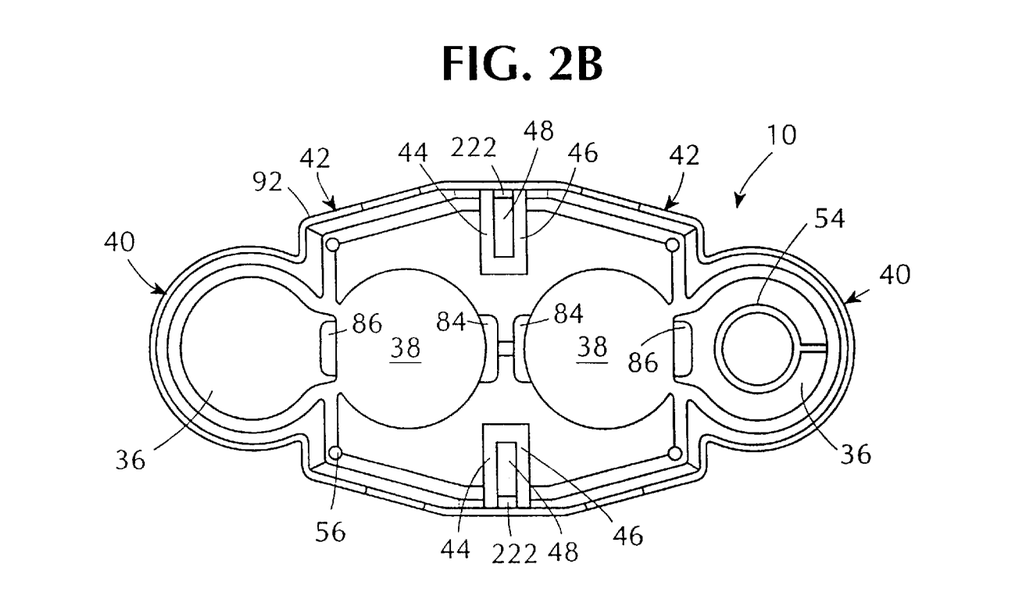
FIG. 2B is a bottom plan view therof.
Figure 3:
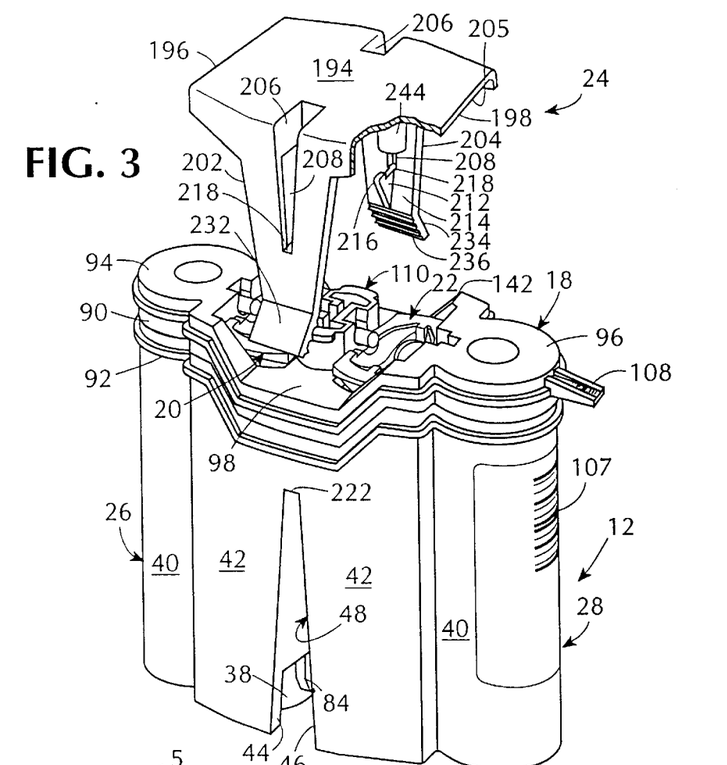
FIGS. 3 and 4 are perspective views prior to and after assembly of the locking clip to the reagent package.
Figure 4:
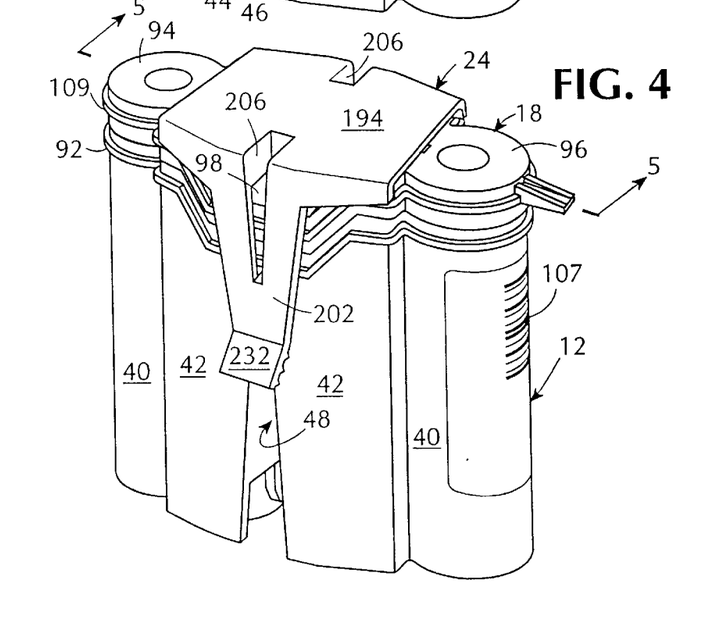

Opposite sides of the container housing portions 42, 42 (FIGS. 2A and 11) include converging inclined portions 44 and 46 that extend upwardly from the lower stepped bases 38, 38 (FIG. 1) and merge into a slot 48. As shown in FIGS. 2B and 5, an orientation sleeve 54 for the reagent package 10 depends from one of the upper stepped bases 36. Base pads 56 are provided at the lower stepped base sections 38, 38.

The glass ampoule 14 is a known closed cylindrical structure, fusion sealed at one end 57 and contains a reagent 58 (FIGS. 5 and 8) which is preferably in a dry lyophilized form to ensure that the reagent 58 remains stable for at least a two-year shelf life, for example. The glass ampoule 14 is designed to be broken under a predetermined pressure applied to each cylindrical portion 40 of the housing section 12.

Each filter screen member 16 is preferably made of a plastic material such as polypropylene and is in the form of hollow cylinder having an upper open end 60 (FIG. 1) with an upper reinforcing ring 62 of imperforate plastic. An opposite lower end 64 of the screen member 16 is of imperforate cup-shaped form. Two oppositely disposed fracture resistant imperforate vertical sections 66 and 68 extend from the upper open end 60 to the cup-shaped end 64. The imperforate vertical sections 66 and 68 are spaced by two oppositely disposed perforate vertical plastic sections 70 and 72. The filter screen member 16 can be formed in any suitable known manner such as by insert molding wherein a hollow completely perforate cylindrical form characteristic of the perforate vertical sections 70 and 72 is initially molded. The imperforate portions 64, 66 and 68 are then molded over predetermined perforate portions of the hollow cylindrical form.

The cup-shaped imperforate base section 64 of each filter screen 16 is formed with oppositely disposed V-shaped keying members 76 and 78. A detent dimple 80 is located midway between the keying members 76 and 78 on one side of the filter screen member 16.

Figure 9:
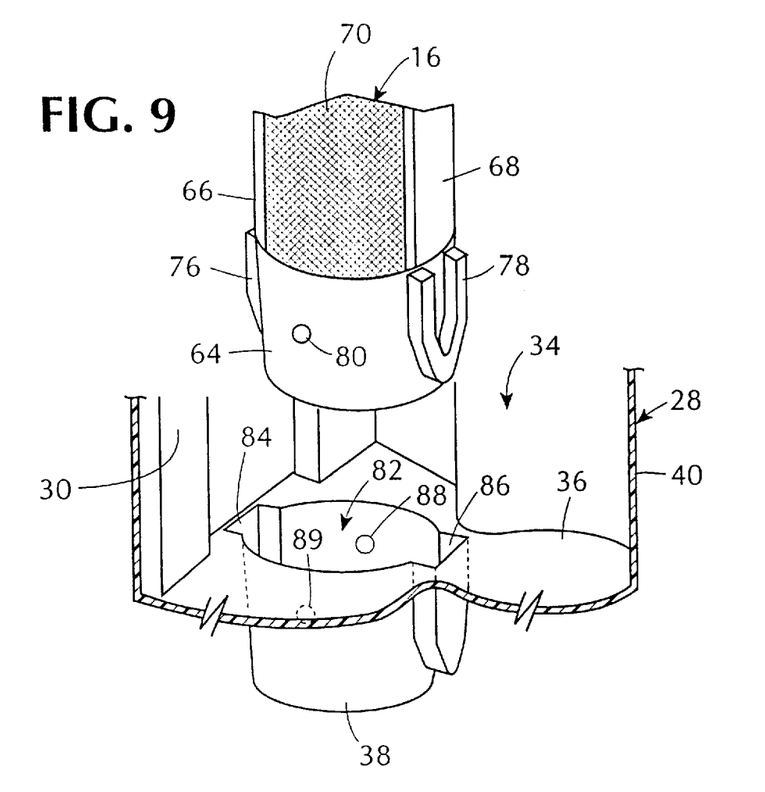
FIG. 9 is an enlarged fragmentary perspective view of a filter screen prior to insertion in a positioning well of the reagent package.
Figure 10:
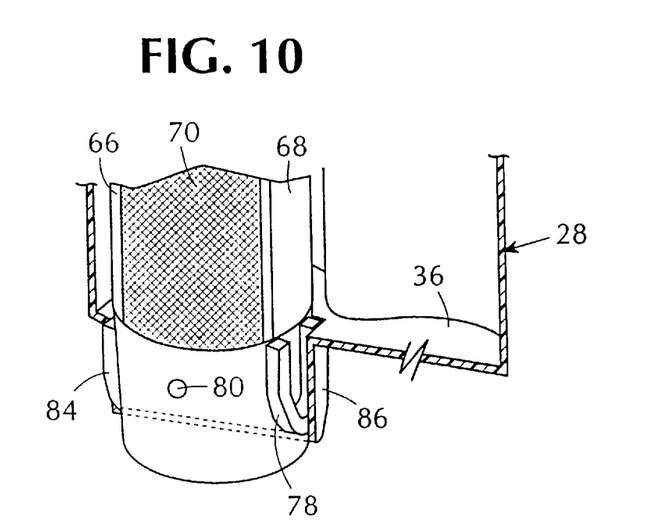
FIG. 10 is a view similar to FIG. 9 with the filter screen located in the positioning well.

Referring to FIG. 9, a positioning well 82 is formed at the lower step 38 of each of the chambers 32 and 34. The positioning well 82 includes opposite keyway slots 84 and 86 of complementary size and shape relative to the keying members 76 and 78 to locate the lower end 64 of the filter screen member 16 in a predetermined axial orientation in the respective container chambers 32 and 34. The positioning well 82 also includes opposite dimple recesses 88 and 89, one of which receives the detent dimple 80 on the filter screen 16. Engagement of the detent dimple 80 with one of the dimple recess 88, 89 detents the filter screen member 16 in the positioning well 82. Thus when the keying members 76 and 78 engage the keying slots 84 and 86 one of the fracture resistant imperforate vertical sections 66 and 68 of the filter screen member 16 can always be positioned adjacent the frangible ampoule 32 as most clearly shown in FIGS. 1, 5, and 8.

Referring to FIGS. 5, 8, 9 and 10 the cup-shaped imperforate lower end 64 of the screen member 16 occupies substantially the entire volume of the well 82. In addition the cup-shaped lower end 64 extends to the upper base portion 36 of each of the packaging sections 26 and 28. Under this arrangement little or no fluid can seep between the well 82 and the lower end 64 of the screen member 16.

With the filter screen members 16, 16 and the frangible ampoules 14, 14 located in the chambers 32 and 34, the container lid member 18 can be positioned on a top peripheral edge 90 (FIG. 1) of the container housing section 12. A peripheral gripper flange 92 is formed around the container housing section 12 slightly below the top edge 90 to facilitate sealing of the lid member 18 to the housing section 12. If desired the width of the flange 92 can be broadened or narrowed at selected locations.

The lid member 18 is a stepped structure with generally circular upper stepped end sections 94 and 96 joined to a lower stepped section 98 by risers 102 and 104. A weight reduction recess 106 is formed in each of the upper sections 94 and 96, and a position flag 108 (FIG. 1) projects beyond one end of the lid member 18 at the upper section 96. A bar code label 107 is provided on the container portion 40 below the position flag 106. A peripheral gripper flange 109 is formed around the outside border of the lid sections 94, 96 and 98, slightly above a lower peripheral edge 111 of the lid member 18. If desired the width of the flange 109 can be broadened or narrowed at selected locations. The gripper flange 109 on the lid member 18 cooperates with the gripper flange 92 on the container housing section 12 during securement of the lid member 18 to the housing section 12.

Figure 22:
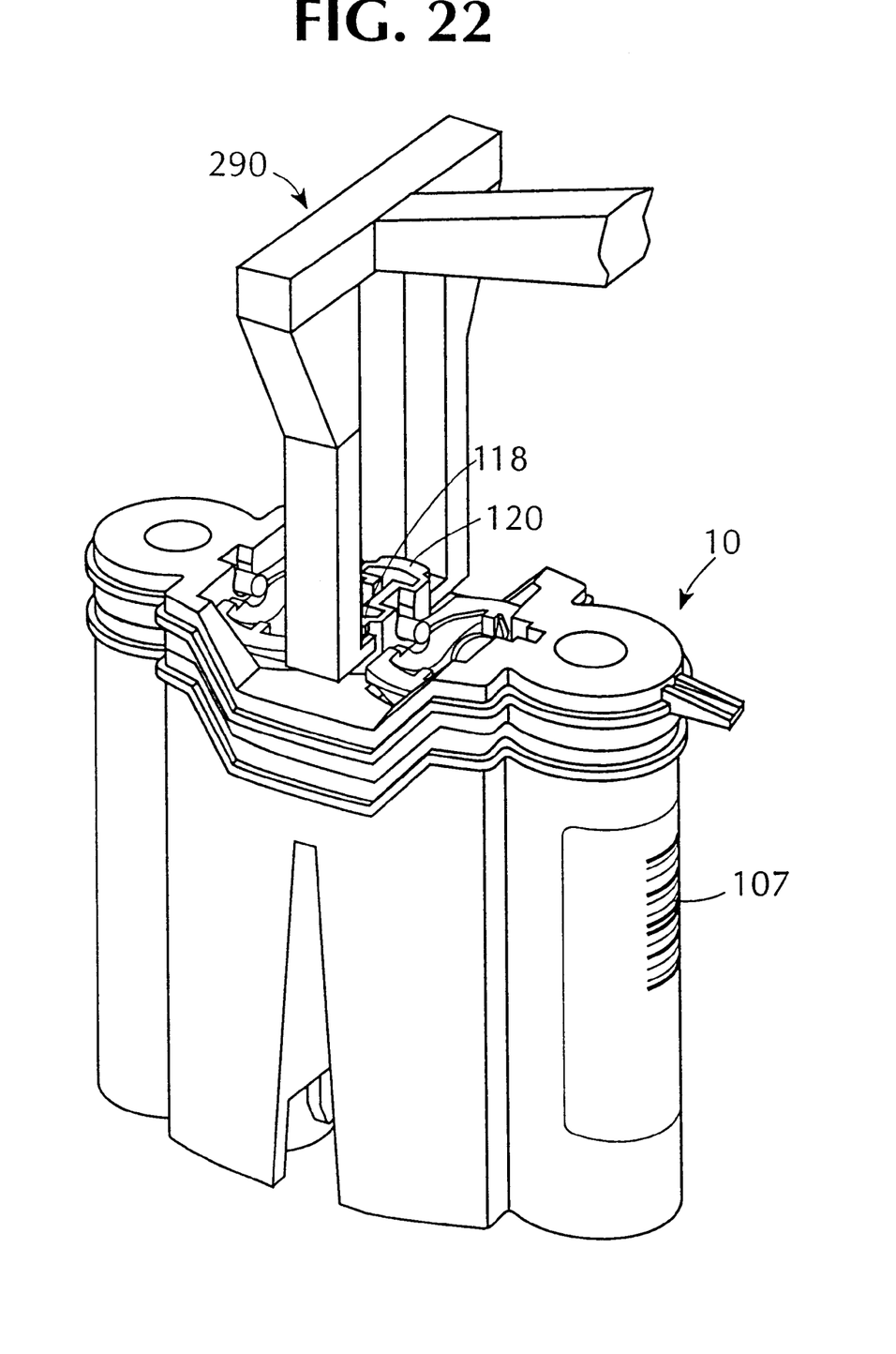

A pivot block 110 extends upwardly from the lid section 98 and includes side walls 112 and 114 spaced from the respective risers 102 and 104. The pivot block 110 also includes horizontal top flanges 118 and 120 for engagement with a robot device 121 (FIG. 22) and a weight reduction recess 116. A first pivot cradle 122 is formed in the riser 102 and a second pivot cradle 124 is formed in the side wall 112 of the pivot block 110 directly opposite the first pivot cradle 122 to accommodate the rocker valve 20. The second pivot cradle 124 includes a wide slot portion 126 (FIG. 5) and a narrow slot portion 128.

A first pivot cradle 136 similar to the first pivot cradle 122 is formed in the side wall 114 of the pivot block 110 and a second pivot cradle 138, similar to the second pivot cradle 124, is formed in the riser 104 directly opposite the first pivot cradle 136 to accommodate rocker valve 22. Corner strengthening gussets 142 are provided at opposite side ends of the risers 102, 104 and the lower section 98 of the lid member 18.

First and second lid openings 144 and 146 extend through the lower section 98 of the lid member 18 between the pivot block 110 and the risers 102 and 104. Each of the lid openings 144 and 146 is surrounded by an O-ring 148. The lid openings 144 and 146 extend through identical collars 152 and 154 (FIGS. 5 and 8) that depend from the lower lid section 98. Each of the collars 152 and 154 has a set of four depending fingers 156 that are equally spaced around the periphery of the openings 144 and 146. A necklace formation of spaced venting recesses 158 (FIG. 5) are formed in the outer peripheral surface of the collars 152 and 154 and the fingers 156.

The collars 152, 154 and the depending fingers 156 are sized to snugly engage the upper open end 60 of each filter screen 16 when the lid member 18 is positioned on the top portion of the container housing 12. The venting recesses 158 ensure that there is a vent between the collars 152, 154 and the filter screen 16 when the collars 152, 154 and their depending fingers 156 engage the open end 60 of the filter screen 16.

A stub-like projection 162 (FIG. 5) depends from an undersurface 164 of the pivot block 110 intermediate the collars 152 and 154. The projection 162 extends across the under surface 164 in alignment with the partition wall 30 of the housing section 12.

The lid member 18 supports the two rocker valves 20 and 22 for pivoted movement in side-by-side spaced relationship. Since each rocker valve 20 and 22 is identical, only the rocker valve 20 will be described in detail.

Referring to FIGS. 1, 7 and 8 the rocker valve 20 includes a curved valve face 166 having stop flanges 168 and 170 provided at respective opposite ends 174 and 176 of the valve face 166. A valve opening 172 in the valve face 166 is closer to the valve end 176 than it is to the valve end 174. A pair of valve pivots 178 and 180 project laterally from respective spaced resilient valve support arms 182 and 184. The valve support arms extend from the stop flange 170 towards the stop flange 168. The valve pivots 178 and 180 are thus cantilevered and can deflect with the valve support arms 182 and 184 toward and away from the valve face 166.

The valve pivot 178 is of uniform diameter whereas the valve pivot 180 is diametrically similar to the pivot 178 but also includes a reduced diametrical section 186 to ensure that the rocker valves 20 and 22 are positioned on the lid 18 in only one predetermined orientation.

Once the rocker valves 20 and 22 are mounted with the same orientation on the lid member 18, the valve pivot 178 of the rocker valve 20 engages the pivot cradle 122 and the valve pivot 180 engages the pivot cradle 124. The valve pivots 178 and 180 of the rocker valve 22 similarly engage the pivot cradles 136 and 138. A slightly narrowed portion 188 (FIGS. 1 and 2A) of the pivot cradles 122, 124, 136 and 138 helps detent the valve pivots 178 and 180 of each rocker valve 20,22 in their respective pivot cradles.

Under this arrangement, the rocker valves 20 and 22 are pivotally supported on the lid member 18, and the curved valve face 166 makes surface contact with the O-ring 148 that surrounds each of the lid openings 144 and 146. Thus, the curved valve face 166 and the O-ring 148 cooperate to provide a first vapor tight seal around the lid openings 144 and 146. When, the rocker valve 20 is pivoted in a first direction by pushing downwardly on the flange 170 the curved valve face 166 moves relative to the lid opening 144 from a valve open position (FIGS. 7 and 12), wherein the valve opening 172 aligns with the lid opening 144, to a valve closed position (FIG. 14) wherein an unopen portion 190 of the curved valve face 166 blocks the lid opening 144.

To assemble the reagent package 10, the filter screens 16, 16 and the glass ampoules 14, 14 are positioned in the respective chambers 32 and 34 of the container housing section 12. The lid member 18 with the rocker valves 20 and 22 pivotally supported thereon is placed on the top edge 90 of the container housing section 12. The gripper flanges 92 and 109 are gripped together in any suitable known manner to provide a pressure contact between the top edge 90 of the housing section 12 and the lower edge 111 of the lid member 18 (FIG. 5). A pressure contact is also made between a top edge 31 of the partition wall 30 and an aligned lower edge 163 of the stub-like projection 162 of the lid member 18 (FIGS. 5 and 8).

The lid member 18 and the container housing section 12 are sealed together using any suitable known sealing means such as hot plate welding. Under this arrangement, a leak-tight seal is provided between the container housing section 12 and the lid member 18. In addition, a leak-tight seal is provided between the top edge 31 of the partition wall 30 and the lower edge 163 of the stub-like projection 162 that depends from the undersurface 164 of the pivot block 110. The container chambers 32 and 34 are thus separately sealed and cannot communicate with each other.

In order to ensure that the weld between the container housing section 12 and the lid member 18 is leak tight a pressure test can be performed with pressure applied through the rocker valves in the valve open position. Pressure is transmitted in any suitable known manner to the inside chambers 32 and 34 of the reagent package and a leak check is performed around the weld portion to determine if there are any leaks.

Figure 14:
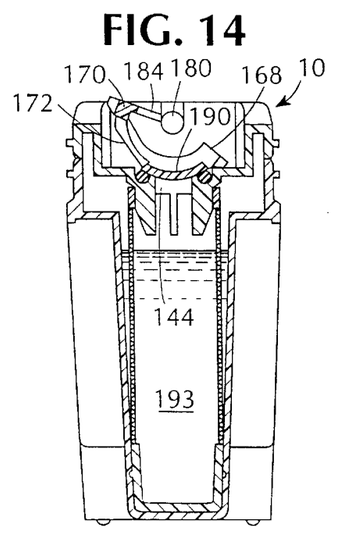

Once the lid member 18 and the container housing section 12 are sealed together, the lid openings 144 and 146 are the only openings to the chambers 32 and 34, and outside access to the lid openings 144 and 146 is controlled by the rocker valves 20 and 22. In the valve closed position the valve face 166 is resiliently forced against the O-ring 148 by the resilient valve support arms 182 and 184 to block the lid openings 144 and 146 and provide a vapor tight seal of such openings (FIG. 14). Thus when the rocker valves 20 and 22 are in the valve closed position the container chambers 32 and 34 are closed.

Figure 12:
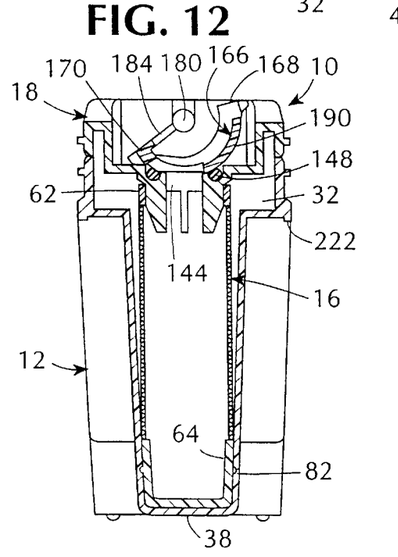
FIGS. 12–15 are sectional views corresponding to FIG. 7 showing the reagent package with the rocker valve in an open position (FIG. 12), infusion of liquid into the reagent package through the open rocker valve (FIG. 13), closing of the reagent package by movement of the rocker valve to a valve closed position (FIG. 14) and locking of the rocker valve in the valve closed position with the locking clip (FIG. 15)

The rocker valves 20 and 22 can be pivoted from the valve closed position of FIG. 14 to the valve open position of FIG. 12 by pushing downwardly on the flange 170 to pivot the valve face 166. In this manner, the valve opening 172 of each rocker valve 20, 22 aligns with the lid openings 144, 146 for example, to permit access to the container chambers 32 and 34.

Figure 13:
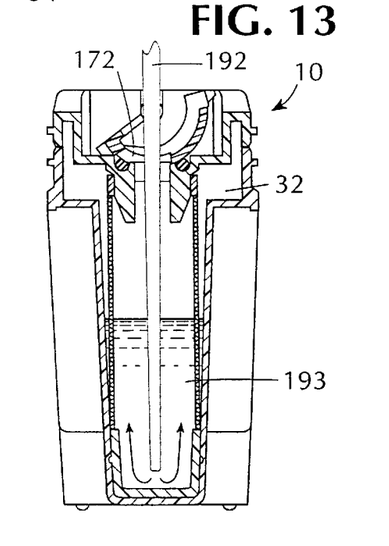

When the rocker valves 20 and 22 are in the valve open position such as shown in FIG. 13 fluid can be dispensed into the container chambers 32 and 34 with a dispensation probe 192 (FIG. 13).

When a requisite amount of liquid is dispensed into the respective container chambers 32 and 34 through the aligned valve and lid openings 172, 142, and 172, 144 the rocker valves 20, 22 are pivoted to a valve closed position to provide a vapor tight seal. Pivoting of the rocker valves 20 and 22 is accomplished by pressing down upon the valve stop flanges 168, 168 until they engage the lower section 98 of the lid member 18.

The vapor tight seal between the valve faces 166, 166 and the lid openings 144 and 146 is further enhanced, especially for shipping and storage purposes, by applying the locking clip member 24 to the reagent package 10.

The locking clip 24 includes a generally rectangular bridge section 194 (FIG. 1) having opposite end portions 196 and 198 and oppositely disposed depending resilient arms 202 and 204. A generally rectangular hollow gusset 206 joins the upper middle portion of each arm 202, 204 and also joins an undersurface 205 (FIG. 5) of the bridge section 194. An elongated vertical opening 208 in each arm 202, 204 aligns with the gusset 206.

The arms 202 and 204 also include a triangular locking flange 212 that projects from an inside surface 214 of the spring arms 202 and 204 at a lower end of the vertical opening 208. A detent prong 216 is provided at an upper edge 218 of the locking flange 212 to engage a detent projection 222 (FIG. 6) that projects downwardly from an upper end of the slot 48 of the container housing section 12.

The clip arms 202 and 204 also include diverging gripper end portions 232 and 234 having knurled formations 236 at the inside surface 214 that constitute a grasping surface.

Figure 6:
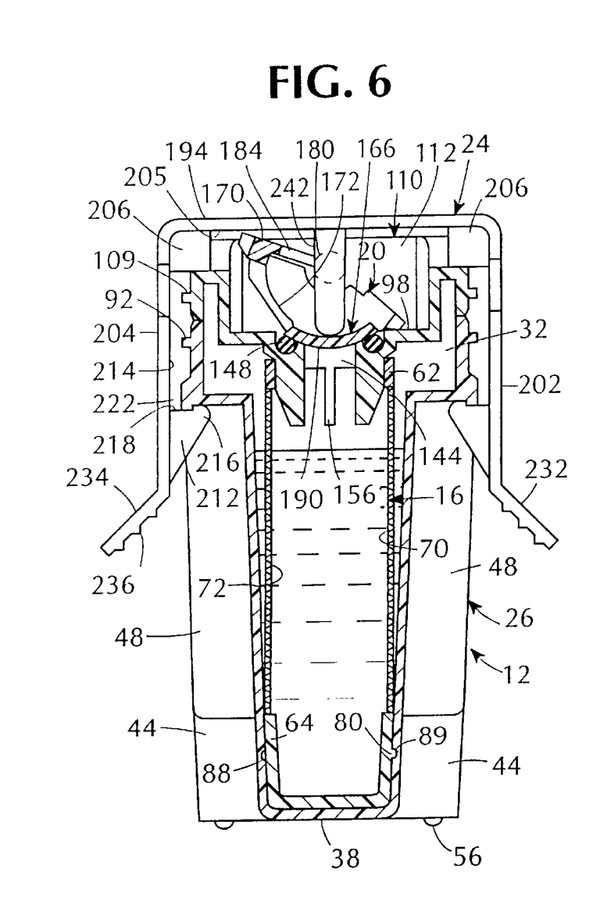
FIG. 6 is a sectional view thereof taken on the line 6—6 of FIG. 5.

The locking clip member 24 further includes a pair of spaced cylindrical pins 242 and 244 (FIGS. 1, 5 and 6) that depend from the bridge section 194 for engagement against the upper surfaces 246, 246 of the valve faces 166, 166 as shown in FIGS. 5 and 6. Although not shown a flat portion can be provided on the upper surface 246 of the curved valve face 166 to engage the free end of the cylindrical pins 242 and 244. The cylindrical pins 242 and 244 thus constitute valve face engagement members.

Figure 15:
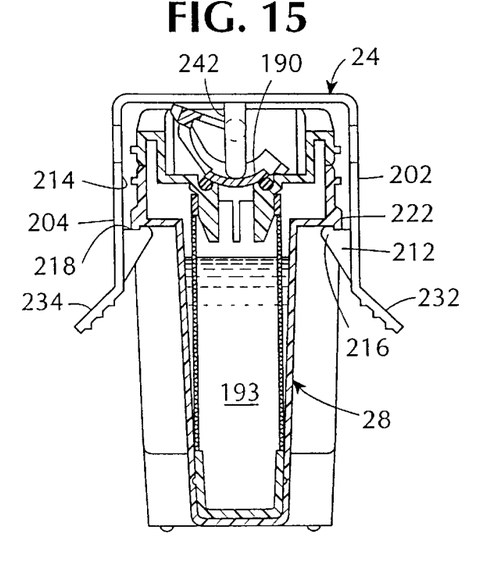
Figure 16:
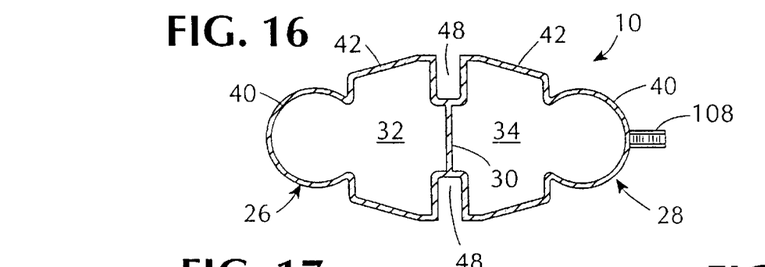
FIG. 16 is a simplified schematic top plan sectional view thereof without the filter screen and glass ampoule.
Figure 17:
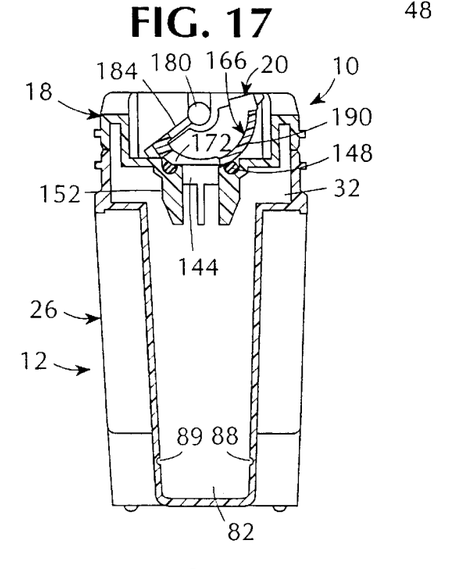
FIGS. 17–20 are sectional views in elevation of the reagent package, without the filter screen and glass ampoule, showing the rocker valve in an open position (FIG. 17), infusion of liquid into the reagent package through the open rocker valve (FIG. 18), closing of the reagent package by movement of the rocker valve to a valve closed position (FIG. 19) and locking of the rocker valve in the valve closed position with the locking clip (FIG. 20)

When the locking clip 24 is installed onto the reagent package 10 the locking flanges 212 on each of the clip arms 202 and 204 engage the detent projections 222 at opposite sides of the container housing section 28 as shown in FIG. 15. The cylindrical pins 242 and 244 thus exert a downward force on the upper surface 246 of the valve face 166 to compress the O-ring 148 and provide an enhanced pressure seal between the valve face 166 and the O-ring 148. The enhanced pressure seal between the valve face 166 and the O-ring 148 is attributable to downward deflection of the valve face 166 by the cylindrical pins 242 and 244, due to the cantilever arrangement of the valve pivots 178 and 180. The amount of deflection of the curved valve face 166 is a function of the length of the cylindrical pins 242 and 244. Preferably the pins 242 and 244 are at least a height that is sufficient to maintain the under surface 205 of the bridge section 194 elevated from the top surface end sections 94 and 96 of the container lid 18. The locking clip member 24 also serves as a shipping cover for the reagent package 10 and if desired the bridge section 194 of the locking clip 24 can be used to accommodate a label or any other package indicia.

An assembled reagent package 10 with the glass ampoules 14, 14 and the filter screen members 16, 16 can receive a reconstituting liquid in each of the chambers 32 and 34. Since the liquid installation operation for each packaging section 26 and 28 is similar, the description of this operation will focus on the packaging section 26.

Figure 11:
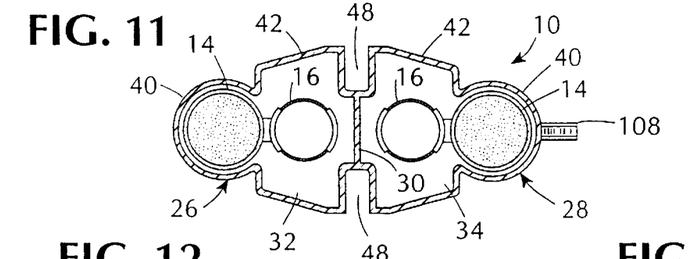
FIG. 11 is a simplified schematic top plan sectional view of the reagent package.

Referring to FIGS. 11 and 12 the rocker valve 20 is pivoted into an open position. A predetermined amount of reconstituting liquid 193 is dispensed by the dispensation probe 192 through the open rocker valve 20 into the chamber 32. When liquid dispensation is completed the rocker valve 20 is pivoted to the valve closed position of FIG. 14 to provide a vapor tight seal of the chambers. Suitable labels (not shown) can be applied to the surface of the reagent package at the cylindrical portion 40 or the trapezoidal portion 42.

The locking clip 24 is then installed onto the reagent package 10 with the rocker valve in the valve closed position as shown in FIG. 15. The pressure enhanced valve seal provided by the locking clip 24 can enable the contents of the reagent package 10 to be adequately stored under refrigeration for up to two years without degradation.

Figure 20:
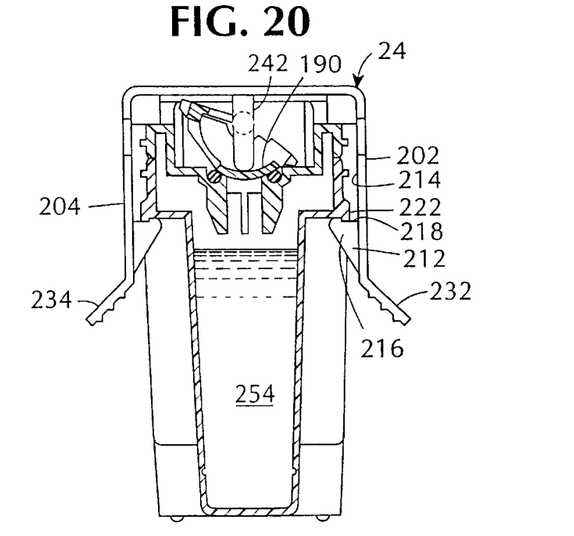

It should be noted that when the locking clip 24 is positioned on the reagent package 10 the pressure of the cylindrical pins 242 and 244 on the curved valve surface 166 of the rocker valves 20 and 22 will restrict rotation of the curve valve face from the valve closed position to the valve open position. The bridge section 194 of the locking clip 24 also shields the rocker valves 20 and 22 from outside access and therefore prevents inadvertent movement of the rocker valves 20 and 22 from the valve closed position. Thus the reagent package 10 can be freely handled when the locking clip 24 is installed as shown in FIG. 20.

When the reagent package is ready to be used in a sample analysis system (not shown), the locking clip 24 is removed and the reagent package 10 is positioned at a known activation device of the sampling system (not shown). The activation device prepares the reagent package 10 for further processing in the sample analysis system. For example the activation device can "exercise" the locked valves 20 and 22 by opening and closing the valves a few times since they have been in a compressed state for the duration of their storage. The rocker valves 20 and 22 can then be easily pivoted due to the cantilevered arrangement of the valve pivots 178 and 180 which exert a slight downward resilient force of the face 166 against the O-rings 148.

A known bar code reader device 300 (FIGS. 1 & 21) can read the bar code label 107 on the reagent package 10 and determine from information in the bar code whether the package has ampoules or has only liquid. The type of reagents contained in the package 10 can also be determined by the bar code reader device 300. The flag portion 108 provides a physical distinguishing feature that facilitates proper orientation of the reagent package 10 in the sample handling and reagent trays (not shown) and locating a "home" position of the reagent package 10.

Figure 21:
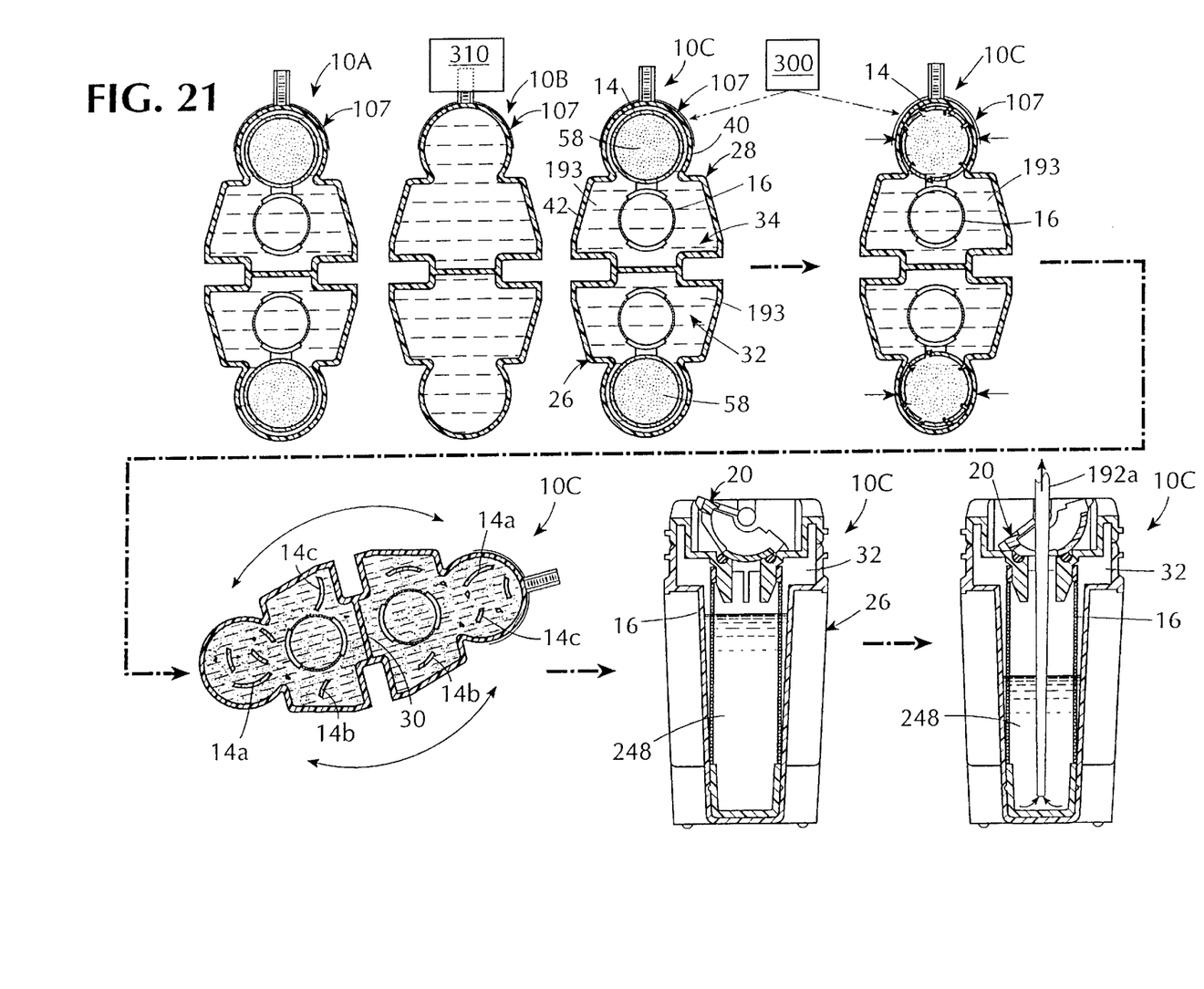
FIG. 21 is a simplified schematic representation of processing steps that include selection of a reagent package from a group, ampoule breakage in a selected reagent package, mixing of ingredients in the selected reagent package and aspiration of the mixed ingredients from the selected reagent package; and, FIG. 22 is a simplified perspective view thereof with a robot device for transporting the reagent package from one location to another.

For example referring to FIG. 21, the bar code reader device 300 can select a particular reagent from an array of reagent packages such as 10A, 10B, and 10C. Based on a reading by the bar code reader device 300 of the bar code labels 107 on the reagent packages 10A, 10B and 10C the bar code reader device 300 will read one of the reagent packages such as 10C. The package 10C is brought, in a known manner to an ampoule activation-breaker device (not shown) that squeezes the cylindrical portions 40 of the packaging sections 26 and 28 until the glass ampoules 14 are broken inside the chambers 32 and 34.

When the ampoule 14 is broken by compressing the outside of the reagent package 10 at the portion 40 the breaking glass is unlikely to puncture the adjacent imperforate portion 68 of the filter screen 16. Other breaking portions of the ampoule 14 are not adjacent the filter screen 16 and therefore do not constitute a danger to the filter screen 16.

During the mixing process, the reagent package is spun and anything that is relatively heavy such as pieces of broken glass 14a, 14b, 14c and 14d tend to move away from the filter screen 16 toward the cylindrical portion 40 of the container housing section 12. Thus since the glass shards from the broken ampoule 14 will tend to move away from the imperforate portions 70 and 72 of the filter 16 there is minimal risk of damage to the filter member 16 by the spinning process. Further, the engagement of the depending fingers 156 of the lid 18 in the upper end 60 of the filter screen 16 holds the top of the filter screen 16 in engagement with the collars 152 and 154. Such engagement prevents any glass shards from entering the filter screen 16 through the upper end 60. Thus there is no opening in the filter screen member 16 for broken glass to enter.

Breakage of the ampoules 14 will enable the lyophilized ampoule ingredients 58 to mix with the reconstituting liquid 193 inside the chamber. The reagent package 10 is spun back and forth automatically by the same ampoule-activator device (not shown) to mix the ingredients inside the chamber until a desired amount of mixing is obtained resulting, in a reagent solution 248.

The reagent package 10 is preferably spun several times in one direction, stopped and then spun in a reverse direction. This spinning procedure can be repeated several times in order to obtain complete mixing of the released material from the ampoule with the reconstituting liquid inside the chamber. The spinning process causes the liquid to climb up the sides of the package and dissolve any powder that may adhere to the upper wall portions of the chambers 32 and 34 when the ampoule 14 is broken.

The mixing cycle for each reagent package can be different depending upon the type of reagent and the type of liquid in the chambers 32 and 34. Therefore the spinning cycles in opposite directions and the amount of repetition of the spinning cycles can be separately determined for packages with different reagents.

When mixing of the package ingredients is completed a robot will pick up the reagent package 10 and move it to an appropriate reagent tray (not shown). Based on information in the bar code label 107 the ampoule activator device can be directed to transport the reagent package to a predetermined reagent tray (not shown).

When the reagent package 10 is located in a selected reagent tray it is oriented such that the flag 108 faces a predetermined direction for use as an optical triggering device to help facilitate precise orientation of the reagent package 10 to an aspiration position. A predetermined amount of the reagent solution 248 is aspirated for test purposes by an aspiration probe 192a that is protracted, in any suitable known manner, into the chamber 32 for example through the rocker valve 20 when the rocker valve 20 is in the valve open position. It should be noted that the probe 192a is preferably a liquid level sensing probe such that the amount of probe projection in the chamber 32 is just enough to go below the surface of the reagent solution 248 in the chamber 32.

The probe 192a upon entering the chamber 32 through the open valve 20 projects into the hollow space or chimney of the filter screen 16. The liquid drawn into the probe 192a is thus protected by the filter screen 16 from any glass shards 14a, 14b, 14c. The filter screen 16 thus filters out and prevents any glass from the broken ampoule 14 from passing to the inside or chimney section of the filter 16. The liquid mixture in the chamber 32 thus, enters the chimney section of the filter screen 16 without glass shards 14a, 14b, 14c from the ampoule 14.

The bar code label 107 on the reagent package can also indicate the number of aspirations intended for the reagent package 10. The number of aspirations corresponds to the number of tests that the reagent package will support. A bar code reading can thus be obtained at the fill stage of the reagent package indicating the intended test capacity of the reagent package 10. Based on such reading the amount of materials 58 and 193 initially placed in the package can be predetermined to ensure that there is little or no wasted reagent solution 248.

As previously noted the lower end 64 of the screen member 16 occupies the lowest portion of the package 10 at the positioning well 82. Thus the aspiration probe 192a can reach down to the lower end 64 of the filter screen 16 to extract substantially all of the liquid reagent solution 248 that is in the reagent package 10 thereby preventing any waste of reagent solution 248.

Based on information in the bar code label 107 as to the number of tests encoded in the package 10 the sample analysis system monitor (not shown) can count the number of test doses of fluid aspirated from the reagent package 10. Thus the sample analysis system can keep an ongoing record of how many test doses have been obtained from the reagent package 10 and cease aspirations when a predetermined number of test doses are obtained.

When the contents of the reagent package are depleted, the package is transported to an exit position of the reagent tray (not shown). A robot 290 (FIG. 22) can then grasp the flanges 118 and 120 on the container lid 18 to lift the reagent package 10 and transport it to a waste receptacle (not shown).

In some instances because of test requirements the reagent package 10 need only contain a premixed liquid reagent solution. Therefore there is no need to include the glass ampoules 14 and the filter screens 16 in the reagent package 10. The reagent package 10 is thus arranged in the manner shown in FIGS. 16–20 without the glass ampoules 14, and without the filter screens 16.

Figure 18:
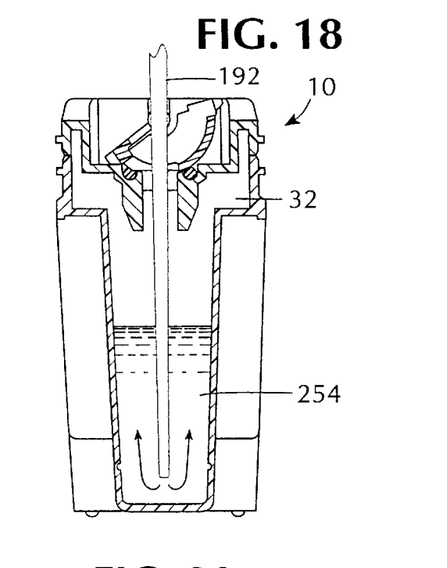
Figure 19:
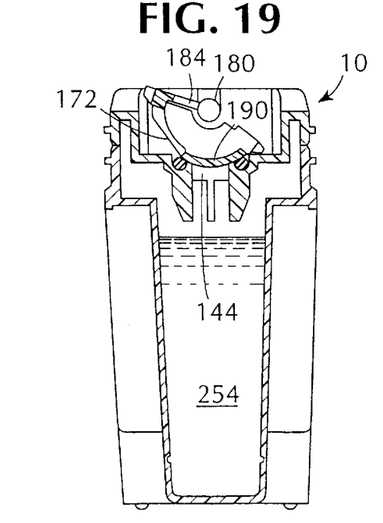

A reagent liquid solution 254 is dispensed into the reagent package 10 through the valve opening 172 when the rocker valve 20 is in a valve open position (FIG. 18). When a predetermined amount of liquid has been dispensed into the reagent package 10 the rocker valve 20 is pivoted to a valve closed position as shown in FIG. 19 and the package 10 is provided with the locking clip 24 to provide an enhanced seal that prevents any outside gases from entering the chambers 32 and 34. Appropriate labels and bar coding are applied to the reagent package 10 in a manner similar to that previously described.

The reagent package 10 of FIG. 20 with liquid reagent only can be stored under refrigeration for approximately two years. When use of the reagent package 10 is desired the user removes the locking clip 24 to reduce the pressure on the rocker valves 20 and 22.

With the locking clip 24 removed from the reagent package 10 the rocker valves 20 and 22, after initial exercise movement, can be easily pivoted from the valve open position to the valve closed position and vice versa.

The reagent package 10 without the filter screen and glass ampoule also permits utilization of all liquid in the chambers 32 and 34 since the positioning well 82 in each chamber represents the lowest point of the reagent package 10. This lowest point of the reagent package 10 aligns with the valve controlled opening 142 of the reagent package 10. Thus the aspiration probe is directed toward the lowest point of the package when the aspiration process is being performed.

The two different chambers 32 and 34 of the reagent package permit containment of different reagents to carry out two different assays. However the reagent package can be provided as a single chamber structure wherein the partition wall 30 would become an outside wall. The lid member of the single chamber reagent package would have an end at the pivot block 110.

It should be noted that the robot always picks up the reagent package for transport when the rocker valves are in a valve closed position, which minimizes the possibility of interference between the robot fingers and the flanges 118 and 120 on the pivot block that are provided for engagement with the robot fingers.

Since the flag 108 and the location sleeve 54 at the base 36 are on the same end of the reagent package, the package can be oriented in a predetermined direction to ensure that the correct reagents are placed in each chamber during filling and that a record can be made in the bar code information 107 as to which chamber contains which reagents.

Robot handling of the reagent package can also be accomplished with robot finger engagement at the slot 48. The inclined surface portions 44 and 46 at the base of the container 12 facilitate positioning of the robot fingers in the slot 48.

Some advantages of the present invention evident from the foregoing description include a reagent package that permits self contained storage of one or more reagent components maintained separately from each other until use of a reagent mixture is desired. A further advantage is that the opening to the container is valve controlled permitting easy opening and closure of the container. The valve has the capability of providing a container seal of variable tightness such as a vapor tight seal in one instance and an enhanced pressure seal in a second instance when a pressure force is imposed on the rocker valve by the locking clip for the reagent package. Other advantages of the invention include a reagent package that can be easily opened and closed by shifting the rocker valve from a valve open position to a valve closed position. The reagent package includes structural features that permit predetermined orientation of the package to accurately identify the ingredients contained in each chamber of the package. A further advantage is that a filter screen provided in the package includes a fracture resistant section and a perforate section, the fracture resistant section being positionable adjacent a breakable ampoule to minimize the possibility of damage to the filter screen when the ampoule is broken within the container. A keying arrangement on the filter screen ensures that the filter screen is placed in a predetermined orientation within the container. A further advantage is that the container has a well portion that defines the lowest portion of the container. The well portion aligns with an aspiration probe thereby ensuring that all ingredients of the container can be drawn from the lowest portion of the container to eliminate any wasted reagent. The reagent package is structured to be easily handled manually or by a robot. A locking clip for the container locks the valves into a sufficiently leak tight condition that enables the ingredients in the container to be stored for approximately two years under refrigeration without degradation.

In view of the above, it will be seen that the several objects of the invention are achieved and other advantageous results attained.

A various changes can be made in the above constructions and method without departing from the scope of the invention, it is intended that all matter contained in the above description or shown in the accompanying drawings shall be interpreted as illustrative and not in a limiting sense.

What is claimed is:

1. A reagent package comprising,
   a) a container having a chamber for a first liquid ingredient, said container having a lid with an opening to said chamber, and a valve on said lid for controlling the opening to said chamber;
   b) a cylindrical screen member in said chamber, said screen member having one end that is open and aligned with said valve controlled opening,
   c) a frangible ampoule containing a second ingredient, said ampoule being located in said chamber adjacent said screen member, and
   d) a predetermined portion of said container proximate said ampoule being formed of a resilient distortable material to enable said container to be externally squeezed at said predetermined portion to break the ampoule to permit mixing of the first and second ingredients in said chamber, the mixed ingredients being removable from the chamber from within the confines of said screen member through said valve controlled opening.

2. The reagent package as claimed in claim 1 wherein said ampoule and said valve controlled opening are next to each other and are not co-axial and are thereby out of alignment with each other.

3. The reagent package as claimed in claim 1 wherein said container includes two of said chambers and two of said openings in said lid, and first and second valves for respectively controlling each said opening in said lid, each of said chambers being noncommunicable with the other and having one of said cylindrical screen members and one of said frangible ampoules to permit separate mixing of the ingredients in each said chamber when the respective frangible ampoules are broken.

4. The reagent package as claimed in claim 1 wherein said screen member is hollow.

5. The reagent package as claimed in claim 1 wherein said screen member includes a cylindrical perforate portion and a cylindrical imperforate portion extending from said cylindrical perforate portion.

6. The reagent package as claimed in claim 5 wherein said screen member includes two of said cylindrical imperforate portions and said cylindrical perforate portion has opposite ends, and one of said cylindrical imperforate portions is provided at each said opposite end of said cylindrical perforate portion.

7. The reagent package as claimed in claim 1 wherein said screen member and said container are provided with engageable positioning means to control the positioning of said screen member in said container such that said screen member is positionable adjacent said ampoule.

8. The reagent package as claimed in claim 7 wherein said engageable positioning means include a key-like projecting portion on one of said screen member and said container and a recess for the key-like projecting portion on the other of said screen member and said container.

9. The reagent package as claimed in claim 7 wherein said screen member includes a cylindrical perforate portion and a cylindrical imperforate portion extending from said cylindrical perforate portion, and wherein said engageable positioning means of said screen member are on said cylindrical imperforate portion.

* * * * *